(12) United States Patent
Nambu et al.

(10) Patent No.: US 6,527,931 B2
(45) Date of Patent: Mar. 4, 2003

(54) PROCESS FOR PRODUCING AN AMINO ACID-N, N-DIACETIC ACID AND ITS SALTS

(75) Inventors: Nobuyoshi Nambu, Yokkaichi (JP); Masanori Furukawa, Suzuka (JP); Makoto Saito, Kawasaki (JP); Tohru Yamamoto, Kawasaki (JP)

(73) Assignees: Showa Denko K.K., Tokyo (JP); Chelest Corporation, Osaka (JP); Chubu Chelest Co., Ltd., Osaka (JP)

( * ) Notice: Subject to any disclaimer, the term of this patent is extended or adjusted under 35 U.S.C. 154(b) by 0 days.

(21) Appl. No.: 09/983,912

(22) Filed: Oct. 26, 2001

(65) Prior Publication Data

US 2002/0046427 A1 Apr. 25, 2002

Related U.S. Application Data

(62) Division of application No. 09/492,181, filed on Jan. 27, 2000, now Pat. No. 6,334,944, which is a continuation of application No. PCT/JP99/02829, filed on May 27, 1999.

(30) Foreign Application Priority Data

May 27, 1998 (JP) ............................................. 10-146351
May 27, 1998 (JP) ............................................. 10-146352

(51) Int. Cl.[7] .............................. B01D 61/42; C11D 3/33
(52) U.S. Cl. ..................... 204/530; 510/375; 510/480; 510/489; 510/490
(58) Field of Search ..................... 204/530; 510/375, 510/480, 489, 490

(56) References Cited

U.S. PATENT DOCUMENTS 5,268,079 A  12/1993 Gomez et al. ........... 204/186.2
6,221,834 B1 * 4/2001 Yamamoto et al. ......... 510/480
6,334,944 B1 * 1/2002 Nambu et al. .............. 205/435

FOREIGN PATENT DOCUMENTS

| EP | 0 628 655 A1 | 6/1994 | ............. D06L/3/02 |
| EP | 0 658 371 A1 | 12/1994 | ............ B01D/61/44 |
| EP | 0 913 461 A | 5/1999 | ............. C11D/3/33 |
| JP | 55-142100 | 11/1980 | ............. C11D/7/54 |
| JP | 57-64619 | 4/1982 | ............. C07B/29/00 |
| JP | 62-39554 | 2/1987 | ............. C07C/99/00 |
| JP | 6-59422 | 3/1994 | ............. G03C/7/42 |
| JP | 7-26296 | 1/1995 | ............. C11D/7/54 |
| JP | 7-216571 | 8/1995 | ............. C25B/3/00 |
| JP | 9-136807 | 5/1997 | ............. A01N/59/16 |
| JP | 0 9 221 697 | 8/1997 | ............. C11D/7/60 |

* cited by examiner

Primary Examiner—Arun S. Phasge

(57) ABSTRACT

An amino acid-N,N-diacetic acid (AADA) or its salt with an equivalent or less of an alkali metal is produced by reducing, through electrodialysis, alkali metal ions from an aqueous solution of the alkali metal salt of an AADA. By this configuration, an AADA salt can be produced in a much higher yield than conventional equivalents without requiring a regeneration operation of a resin as in the use of an ion exchange resin or without requiring crystallization-separation of crystals of the AADA salt as in the addition of an organic solvent. A salt of an amino acid-N,N-diacetic acid is also produced by reacting an AADA with any of metal oxides, metal hydroxides, metal carbonates, metal hydrogencarbonates, ammonium hydroxide, ammonium carbonate, ammonium hydrogencarbonate or organic amine compounds. By this configuration, a metal salt, aromonium salt or organic amine salt of an AADA can be produced with efficiency without the formation of by-products.

4 Claims, 5 Drawing Sheets

Ⓔ: ELECTRODE SOLUTION
Ⓐ: AQUEOUS ACID SOLUTION
Ⓢ: SAMPLE
Ⓦ: WATER

Ⓔ: ELECTRODE SOLUTION
Ⓐ: AQUEOUS ACID SOLUTION
Ⓢ: SAMPLE

US 6,527,931 B2

PROCESS FOR PRODUCING AN AMINO ACID-N, N-DIACETIC ACID AND ITS SALTS

This is a divisional of application Ser. No. 09/492,181 filed Jan. 27, 2000, the disclosure of which is incorporated herein now U.S. Pat. No. 6,334,944, which is a continuation of International Application PCT/JP99/02829 filed May 27, 1999.

BACKGROUND OF THE INVENTION

1. Field of the Invention

The present invention relates to a production process of an amino acid-N,N-diacetic acid (hereinafter may be referred to as "AADA") or its salt with an equivalent or less of an alkali metal, with efficiency, by reducing alkali metal ions from an aqueous solution of an alkali metal salt of an AADA. To be more specific, it relates to a process of an aqueous solution of an AADA salt low in pH or an acid form of AADA in high yield by reducing alkali metal ions from an aqueous solution of an AADA alkali metal salt, and to a process for producing a salt of an AADA.

2. Description of the Prior Art

Metal salts and amine salts of ethylenediaminetetraacetic acid (hereinafter may be referred to as "EDTA") or diethylenetriaminepentaacetic acid (hereinafter may be referred to as "DTPA") have been used as, for example, detergent additives, trace metal element fertilizers for agricultural use, and photographic agents. In particular, iron salts and ammonium salts of EDTA and DTPA have been used in large quantities as oxidizing agents for color photography printing. These chelate salt compounds are, however, hardly biodegradable, and therefore a variety of highly biodegradable chelate salt compounds derived from material amino acids have been developed as alternatives to these compounds, from the viewpoint of environmental protection in recent years. Among them, AADA salts receive attention for their high biodegradability. Of these AADA salts, glutamic acid-N,N-diacetic acid (hereinafter may be referred to "GLDA") derived from glutamic acid is most demanded.

As production process for AADA salts, processes of reacting a corresponding amino acid with sodium monochloroacetate (Japanese Unexamined Patent Publication No. 6-59422) as a laboratory-scale production process, or with sodium cyanide and formalin (U.S. Pat. No. 2,500,019) as a commercial-scale production process are generally employed. In any process, a solution of an AADA sodium salt is produced which contains sodium ions in large amounts and shows a strong alkalinity. Therefore, the solution shows poor compatibility and cloudiness or precipitates may form when it is mixed with a detergent. Furthermore, such a solution cannot be used as intact as a material for shampoos and other products that will be used with pH value around neutrality.

In addition, for the production of metal salts, ammonium salts and amine salts of an AADA, such an AADA containing sodium ions is generally used as a material and reacted with an inorganic or organic acid. According to this process, however, an alkali metal salt of the inorganic or organic acid is by-produced and thus a high purity chelate metal salt cannot be obtained. In the production of GLDA iron salts, which are important as photographic agents among these metal salts of AADA, an ammonium salt of GLDA is generally reacted as a material with iron nitrate. According to this process, however, by-produced ammonium nitrate in coexistence becomes a problem.

On this account, demands have been made to provide an AADA, which contains no sodium ion, to be used as a material.

In this connection, the acids of EDTA and DTPA, which have been conventionally used, are low in solubility, and crystals of these acids containing no sodium ion can be obtained with facility by adding sulfuric acid or hydrochloric acid to decrease pH. AADA is, however, high in solubility, and crystals of its acid containing no sodium ion can hardly be obtained even by decreasing pH, or if obtained, it is obtained in low yield which invites increased costs.

The following processes have therefore been attempted: a process of adding an inorganic acid to a solution of an AADA sodium salt to acidify the solution, and precipitating and recovering an AADA salt by the use of an organic solvent as a bad solvent; a process of removing alkali metal ions with the use of an ion exchange resin; and a process of adding sulfuric acid to form sodium sulfate and thereby to remove alkali metal ions.

According to the process of precipitating and recovering the AADA salt by the use of an organic solvent as a bad solvent, the solubility of an inorganic salt in coexistence also decreases, which invites the contamination of the inorganic salt in the product AADA. To minimize the contamination of the inorganic salt, the amount of the organic solvent to be added must be decreased, but the yield of the product AADA decreases with a decreasing organic solvent.

The process of using an ion exchange resin is a process to be used as a means for removing a low concentration alkali metal ion but is improper as a means for removing such high concentration sodium ions as in the AADA reaction mixture. This is because a large quantity of an ion exchange resin is required to remove high concentration sodium ions and the resultant resin should be regenerated at frequent intervals, resulting in a deteriorated productivity. In addition, the AADA salt attached to the ion exchange resin is released into a wastewater during the regeneration of the resin, resulting in a very low yield of the AADA salt.

According to the process of adding sulfuric acid to form sodium sulfate and thereby to remove sodium ions, the concentration of sodium ions in an aqueous solution of the AADA salt cannot be reduced to such a low concentration of 3% or less, because sodium sulfate is high in solubility even at low temperatures. In addition, this process is highly disadvantageous in that sulfate ions are contaminated into the aqueous solution of the AADA salt.

The present invention has been accomplished to solve the above problems. Accordingly, it is an object of the invention to provide a process for an alkali metal salt of an AADA salt.

It is another object of the invention to provide a process for metal salts, ammonium salts or organic amine salts of an AADA with efficiency.

A further object of the invention is to provide a process for a solution of a magnesium salt of an AADA with efficiency.

Yet another object of the invention is to provide a bleaching agent composition containing a magnesium salt of an AADA such as mentioned above.

It is another object of the invention to provide a process for a solution of an iron salt of an AADA with efficiency.

A yet further object of the invention is to provide a process for crystals of an ammonium ferric salt of glutamic acid-N,N-diacetic acid with efficiency.

SUMMARY OF THE INVENTION

The invention provides a process for the production of an AADA, represented by the following formula (1), or its salt with an equivalent number or less of alkaline metals, the process includes: reducing alkali metal ions from an aqueous solution of an alkali metal salt of an AADA by electrodialysis.

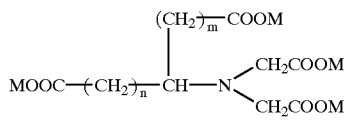

(1)

(wherein M represents an alkali metal, m represents 0 or an integer of from 1 to 2, and n represents 0 or an integer of from 1 to 3)

The invention provide, in another aspect, a process for the production of a salt of an AADA salt, the process includes: reacting an AADA with a compound selected from an metal oxide, a metal hydroxide, a metal carbonate, a metal hydrogencarbonate, an ammonium hydroxide, an ammonium carbonate, an ammonium hydrogencarbonate, or an organic amine compound.

The invention provides, in a further aspect, a process for the production of a magnesium salt of an AADA, the process includes reacting an AADA, which is obtained by electrodialysis, with a compound selected from a magnesium oxide, a magnesium hydroxide, a magnesium carbonate or a magnesium hydrogencarbonate. The invention provides, in yet another aspect, a process for the production of a salt of magnesium compound having an improved hygroscopicity by reacting 0.5 to 1 equivalent of a magnesium compound with 1 equivalent of a carboxyl group.

In another aspect, the invention provides a bleaching agent composition composed of a magnesium salt of amino acid and an oxygen bleaching base.

The invention provides, in a further aspect, a process for the production of a solution of a solution of an iron salt of an AADA, which process includes the steps of electrodialyzing an aqueous solution of an alkali metal salt of an AADA with the use of a hydrogen ion permselective membrane on the anode side and a cation permeable membrane on the cathode side to give an AADA, and reacting the obtained AADA with an iron oxide or metallic iron.

In addition, the invention provides a process for the production of a crystal of an ammonium ferric salt of glutamic acid-N,N-diacetic acid, which process includes adjusting the pH of a solution of an ammonium ferric salt of glutamic acid-N,N-diacetic acid to the range from 2.5 to 5.0 to crystallize and separate an ammonium ferric salt of glutamic acid-N,N-diacetic acid.

The invention further provides a crystal of an ammonium ferric salt of glutamic acid-N,N-diacetic acid.

DETAILED DESCRIPTION OF THE PREFERRED EMBODIMENTS OF THE INVENTION

In a preferred embodiment, the production process of an amino acid-N,N-diacetic acid or its salt with an equivalent number or less of alkaline metal ions has a striking feature of reducing alkali metal ions from an aqueous solution of an AADA alkali metal salt by electrodialysis. The electrodialysis requires neither a regeneration operation of a resin as in the use of an ion exchange resin nor crystallization-separation of crystals of an AADA salt as in the addition of an organic solvent, and can reduce alkali metal ions from the aqueous solution of an AADA alkali metal salt with efficiency.

The electrodialysis utilizes a principle that when positive and negative electrodes are put in an aqueous solution of an electrode solution and an electric potential gradient is applied thereto, positive and negative ions in the solution move toward counter electrodes respectively, and means a treatment of arranging an ion exchange membrane and an semipermeable membrane between both electrodes and carrying both ions in the solution between the membranes in different directions to eliminate the ions out of the membranes.

Figure 1:
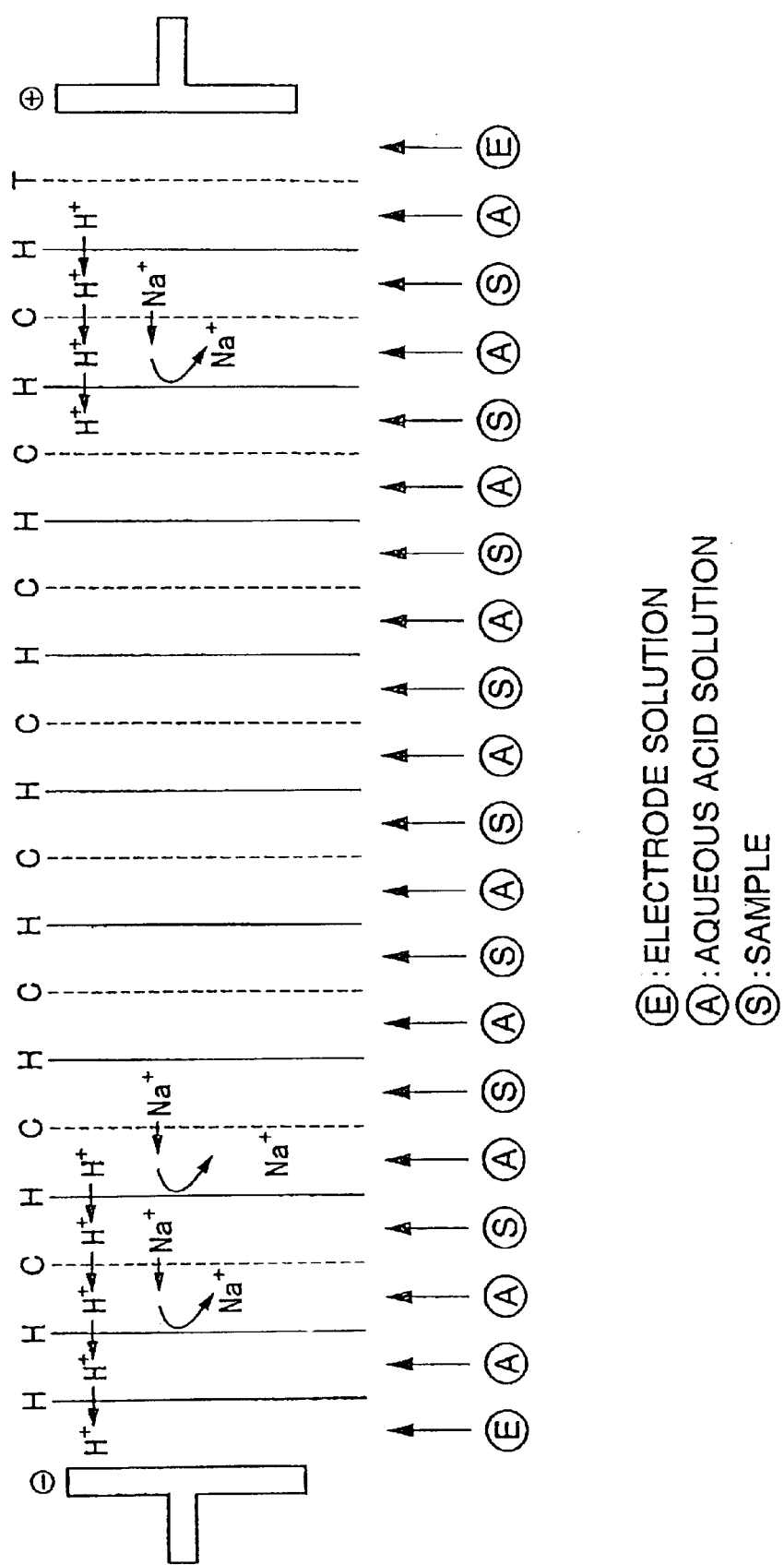
FIG. 1 is a schematic view of an electrodialyzer to be used in the invention.

In another preferred embodiment of the invention, the electrodialysis is performed with a hydrogen ion permselective membrane on the anode side and a cation permeable membrane on the cathode side. According to the electrodialysis to be used as shown in FIG. 1, each membrane cell, through which an aqueous solution of an AADA alkali metal salt (referred to as "sample" in the figure) passes, comprises a hydrogen ion permselective membrane H as a semipermeable membrane on the anode side and a cation permeable membrane C as an ion exchange membrane on the cathode side. On both sides of the hydrogen ion permselective membrane H and the cation permeable membrane C, an aqueous acid solution is respectively fed. In this procedure, alkali metal ions in the aqueous solution of an AADA alkali metal salt move toward a counter electrode, i.e., toward the cathode, and permeate through the membrane C as intact and migrate into the aqueous acid solution, because the permeable membrane on the cathode side is the cation permeable membrane C. Separately, hydrogen ions migrate from the aqueous acid solution on the anode side through the hydrogen ion permselective membrane H to the aqueous solution of AADA alkali metal salt. By this mechanism, alkali metal ions in the aqueous solution of AADA salt are replaced with hydrogen ions to reduce the alkali metal ions in the aqueous solution of AADA salt.

The term "hydrogen ion permselective membrane" as used herein means a functional membrane, through which only hydrogen ions are permeable and other cations or anions are impermeable, and is a hybrid membrane composed of laminated cation exchange membrane and anion exchange membrane. When an electric potential gradient is applied to the membrane, water is decomposed to form hydrogen ions and hydroxide ions, and the hydrogen ions and hydroxide ions move toward cathode side and anode side respectively, and the hydroxide ions react with hydrogen ions in the aqueous acid solution to form water. Thus, only hydrogen ions can apparently permeate through the membrane. As examples of commercially available hydrogen ion permselective membranes, there may be mentioned "Selemion HSV" (manufactured by Asahi Glass Co., Ltd.) and "NEOSEPTA BP1" (manufactured by Tokuyama Corporation).

The term "cation permeable membrane" means a functional membrane through which cations are permeable and anions are impermeable. As the membrane, use can advantageously be made of a membrane which retains, at high densities, sulfonic acid group, carboxylic acid group and other groups which will have a negative charge when dissociated, and is composed of a styrenic polymeric homogenous membrane. Commercially available membranes include, for instance, "Selemion CMV" (manufactured by Asahi Glass Co., Ltd.), "Aciplex CK-1, CK-2, K-101, and K-102" (manufactured by Asahi Chemical Industry Co., Ltd.), "Neosepta CL-25T, CH-45T, C66-5T, and CHS-45T" (manufactured by Tokuyama Corporation), and "Nafion 120, 315, and 415" (manufactured by Du Pont Company). The membrane can be chosen according to the species of the alkali metal salt of amino acid diacetic acid or impurities to be removed.

Figure 2:
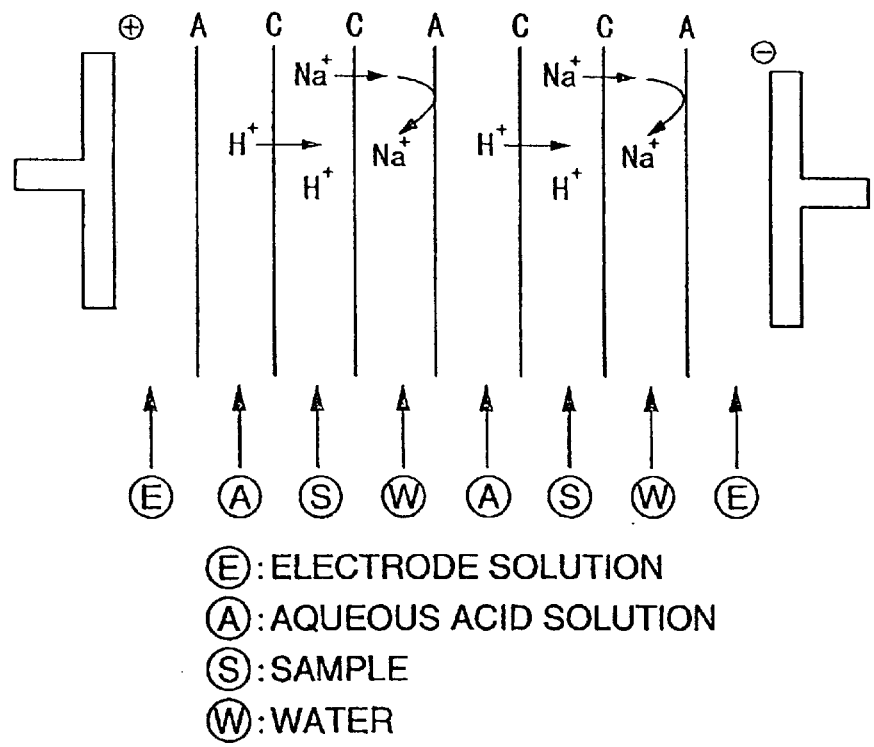
FIG. 2 is a schematic diagram of another electrodialyzer to be used in the invention.

In another preferred embodiment, the electrodialysis is carried out with cation permeable membranes both on the anode and cathode sides. In the electrodialysis to be used in the process as illustrated in FIG. 2, a membrane cell, through which an aqueous solution of an AADA alkali metal salt (referred to as "sample" in the figure) passes, is composed of cation permeable membranes C both as semipermeable membranes on the anode and cathode sides, and an aqueous acid solution is fed to both sides of the cation permeable membranes C. In this procedure, the alkali metal ions in the aqueous solution of AADA alkali metal salt move toward a counter electrode, i.e., toward the cathode, and as the permeable membrane on the cathode side is the cation permeable membrane C, the alkali metal ions permeate through the membrane as intact and migrate into the aqueous acid solution. Separately, hydrogen ions migrate from the aqueous acid solution on the anode side through the cation permeable membrane C on the anode side into the aqueous solution of AADA alkali metal salt. By this mechanism, the alkali metal ions in the aqueous solution of AADA alkali metal salt are replaced with hydrogen ions to reduce the alkali metal ions in the aqueous solution of AADA salt. Concurrently, coexistent low-molecular weight impurities such as glycolic acid, the material amino acid, a sodium halide can be removed.

As the electrodialyzer to be used wherein electrodialysis is carried out with cation permeable membranes both on the anode and cathode sides, any device that has the above configuration can be employed. For example, "Microacilyzer EX3" (manufactured by Asahi Chemical Industry Co., Ltd.) is commercially available and can advantageously be used. As the cation permeable membrane, any suitable cation permeable membrane wherein electrodialysis is performed using a hydrogen ion permselective membrane on the anode side and a cation permeable membrane on the cathode side can also be employed in this process.

In another preferred embodiment, an inorganic or organic acid is added to the aqueous solution of an alkali metal salt of an amino acid having a secondary or tertiary amino group and three or more carboxyl groups to give an alkali metal salt of an inorganic acid or an alkali metal salt of an organic acid, and the resultant aqueous solution is subjected to electrodialysis using an anion permeable membrane on the anode side and a cation permeable membrane on the cathode side.

Figure 3:
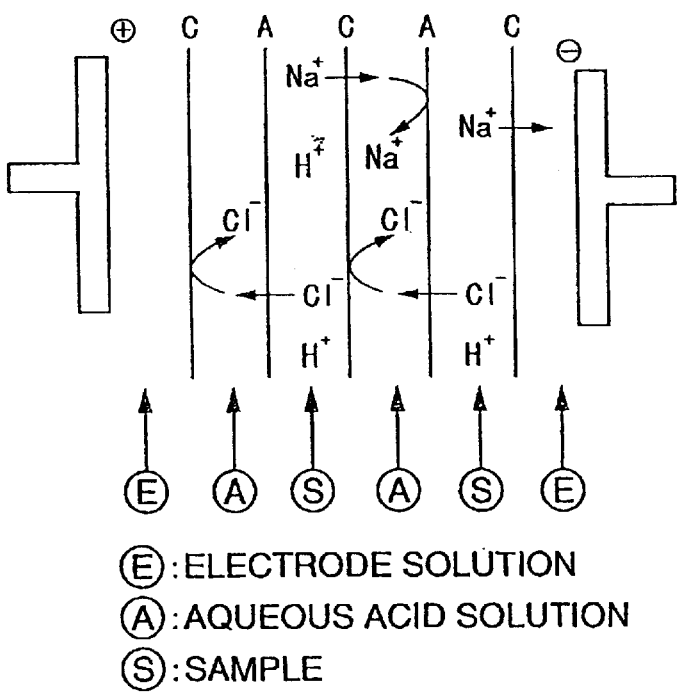
FIG. 3 is a schematic diagram of another electrodialyzer to be used in the invention.

This electrodialysis is advantageous in that alkali metal ions can be removed with efficiency and unnecessary organic anions and inorganic anions can also be removed. As illustrated in FIG. 3, in the electrodialysis to be used in the present invention, each membrane cell, through which an aqueous solution of an AADA alkali metal salt (referred to as "sample" in the figure) passes, comprises an anion permeable membrane A as a semipermeable membrane on the anode side and a cation permeable membrane C as a semipermeable membrane on the cathode side. An aqueous acid solution is respectively fed on both sides of the permeable membranes. In this procedure, the aqueous solution of AADA alkali metal salt, which has been neutralized with the inorganic or organic acid, comprises alkali metal ions, AADA ions, hydrogen ions, and organic or inorganic anions. The alkali metal ions move toward a counter electrode, i.e., toward the cathode, and the alkali metal ions permeate through the membrane C as intact and migrate into the aqueous acid solution, because a permeable membrane on the cathode side is the cation permeable membrane C. Theoretically, hydrogen ions should permeate through the cation permeable membrane C and migrate into the aqueous acid solution in the same manner as the alkali metal ions. However, most hydrogen ions in the aqueous solution of AADA salt are compounded in the amino acid-diacetic acid salt, and remain in the aqueous solution of AADA salt without migrating through the cation permeable membrane C into the aqueous acid solution. As a consequence of this mechanism, alkali metal ions in the aqueous solution of AADA alkali metal salt are replaced with hydrogen ions. Concurrently, the organic or inorganic anions migrate toward a counter electrode, i.e. toward the anode, and as the permeable membrane on the anode side is the anion permeable membrane A, the anions permeate through the membrane A as intact and migrate into the aqueous acid solution. By this configuration, organic or inorganic anions can also be removed from the aqueous solution of AADA alkali metal salt.

The term "anion permeable membrane" used herein means a functional membrane through which anions are permeable and cations are impermeable. To be more specific, it means a membrane through which glycolic acid anions, inorganic anions, sulfuric acid anions, halogen anions, and other low molecular weight anions are permeable but cations and high molecular weight anions are impermeable. As the membrane, use can advantageously be made of a membrane having a positive fixed-charge such as a tertiary ammonium group and be composed of a styrenic polymeric homogeneous membrane. Of such membranes, commercially available membranes include, for instance, "Selemion AMV, and ASV" (manufactured by Asahi Glass Co., Ltd.), "Aciplex CA-1, CA-2, A-101, and A-102" (manufactured by Asahi Chemical Industry Co., Ltd.), "Neosepta AV-4T, AF-4T, AFS-4T, and ACH-45T" (manufactured by Tokuyama Corporation), and "Nepton 61AZL386" (manufactured by Ionics).

As the cation permeable membrane, any of those described herein can be used in the present process.

As the electrodialyzer to be used in the process according to the present inventive process, any device that has the above configuration can be employed, and for example, "Microacilyzer S3" (manufactured by Asahi Chemical Industry Co., Ltd.) is commercially available.

Organic acids to be used for the neutralization in the process include formic acid, acetic acid, and other low molecular weight organic acids that are generally employed. Inorganic acids to be used for the neutralization include hydrochloric acid, sulfuric acid, and other inorganic acids that are conventionally used.

As the acid of the aqueous acid solution to be used in the electrodialysis, there may be mentioned, for instance, sulfuric acid, hydrochloric acid, phosphoric acid, nitric acid, and other inorganic acids, acetic acid, glycolic acid, and citric acid, of which sulfuric acid can advantageously be used for its low costs. The amount of the aqueous acid solution can be calculated based upon the amount of alkali metal ions to be removed. An excess amount of the acid solution invites increased costs as a natural consequence. The aqueous acid solution is preferably used in several installments and is replaced during the electrodialysis, because the use of the whole of the calculated required amount deteriorates the current efficiency. Such an installment use can reduce the concentration of alkali metal ions in the aqueous solution of AADA alkali metal salt with efficiency. The aqueous acid solution may be circulated and recycled.

The concentration of the aqueous acid solution should preferably fall in the range from 1 to 40 wt %. The concentration is more preferably 5 wt % or more, and typically preferably 8 wt % or more for the lower limit, and is more preferably 20 wt % or less, and typically preferably 15 wt % or less for the upper limit. If the concentration of the aqueous acid solution exceeds 40 wt %, excess amounts of sulfuric ions and other bases may migrate into the aqueous solution of AADA salt, and crystals of sodium sulfate or another alkali metal salt may be precipitated to plug the membrane at low temperatures of the solution. On the contrary, if it is less than 1 wt %, the proportion of the circulated aqueous acid solution must be increased, resulting in an increased volume of a reservoir.

The concentration of the aqueous solution of an AADA alkali metal salt should preferably fall in the range from 5 to 60 wt %. The concentration is more preferably 10 wt % or more, and typically preferably 20 wt % or more for the lower limit, and more preferably 50 wt % or less, and typically preferably 40 wt % or less for the upper limit. If the concentration of the aqueous solution of AADA alkali metal salt exceeds 60 wt %, the viscosity of the solution increases to deteriorate the difusibility of the solution and deteriorates the dialysis efficiency per hour. In addition, a pressure applied on the dialysis membranes may become excessively high so as to destroy the membranes, and a pressure between the membranes should be equalized to deteriorate the operativity of the device. On the contrary, the concentration of the aqueous solution of AADA alkali metal salt less than 5 wt % deteriorates the productivity and may require concentration operation after dialysis, and is impractical.

In this connection, when the produced AADA is glutamic acid-N,N-diacetic acid or serine diacetic acid, the aqueous solution of the AADA salt can be treated in high concentrations, as these compounds are highly soluble in water. If complete removal of the alkali metal ions is not required, for example, if half or less the alkali metal ions relative to the equivalency of the AADA should be removed, the produced AADA or its salt is highly soluble in water and it can be treated in higher concentrations.

When almost all the alkali metal ions should be removed from the aqueous solution of AADA alkali metal salt, the concentration must be adjusted beforehand in order to avoid the precipitation of crystals of AADA during the dialysis.

As an electrode solution to be circulated in electrode cells, an acid identical to the acid used for the dialysis is preferably employed, whose concentration is preferably about 1 to 2 wt %. If the concentration of the electrode solution exceeds 2 wt %, electrode plates may be corroded faster. On the contrary, if it is less than 1 wt %, the electric current may hardly flow.

The electrode current in the electrodialysis can be controlled either of a constant voltage method or constant current method. With an increasing current, the required treatment time decreases, but the temperature of the solution increases due to a heat generated by electrification, and the solution must be cooled. Accordingly, the upper limit of the current is preferably controlled so as to maintain the temperature of the solution within the range not deteriorating the membrane.

The electrodialysis operation is generally performed in a batch system, and the aqueous solution of AADA alkali metal salt is exchanged after the completion of each dialysis operation. However, the aqueous acid solution does not need to be exchanged at the same time, and it can be used until in the course of a next batch operation and then replaced with a new portion of the aqueous acid solution. By this operation, the concentration of the alkali metal ions in the aqueous solution of AADA alkali metal salt can be reduced with efficiency. Naturally, the electrodialysis can be performed continuously by connecting a multiplicity of dialyzers to constitute a multistage dialyzer.

In the batch treatment, the completion of the electrodialysis operation should be determined by whether the concentration or pH value of the aqueous solution of AADA alkali metal salt reaches a predetermined value. When the electrodialysis is performed in order to form an AADA aqueous solution from which alkali metal ions are removed, the electrodialysis operation should preferably be completed at the time when the concentration of alkali metal ions reaches the lower permissible limit or below. This is because excessive electrodialysis for the purpose of complete removal of the alkali metal ions deteriorates the current efficiency and increases the amount of sulfuric acid ions and other bases to migrate and contaminate into the AADA solution.

The aqueous solution of an AADA salt obtained by reducing alkali metal ions through electrodialysis contains a trace amount of a base such as sulfuric acid ions. Where necessary, such sulfuric acid ions can be removed by adding barium hydroxide or barium carbonate in a given amount to the solution to form barium sulfate, and removing barium sulfate by filtration.

In the process according to the present invention, the alkali metal salt of amino acid having a secondary or tertiary amino group and three or more carboxyl groups to be electrodialyzed is preferably an alkali metal salt of an AADA. As such a metal salt, an alkali metal salt represented by the formula (1) is more preferred. The metal salts to be used in the present invention include, for example, alkali metal salts of iminodisuccinic acid and alkali metal salts of ethylenediaminedisuccinic acid.

As examples of alkali metal salts of AADA, there may be mentioned alkali metal salts of glutamic acid-N,N-diacetic acid, alkali metal salts of aspartic acid-N,N-diacetic acid, alkali metal salts of glycine-N,N-diacetic acid, alkali metal salts of α-alanine-N,N-diacetic acid, alkali metal salts of β-alanine-N,N-diacetic acid, and alkali metal salts of serine-N,N-diacetic acid. Of these salts, alkali metal salts of glutamic acid-N,N-diacetic acid can advantageously be used.

The aqueous solution of AADA or its salt containing reduced or no alkali metal ion, which is obtained by the above process, is used in the form of AADA metal salts or AADA organic amine salts as materials for detergent additives and for trace element fertilizers in agricultural use. The AADA aqueous solution can be converted into an AADA metal salt by reacting it with, for instance, an elementary metal, metal oxide, metal hydroxide, or metal carbonate. Each of these salts can be used singly or in combination as a mixture.

Next, the invention a process for the production of a salt of an amino acid-N,N-diacetic acid represented by the following general formula (1) wherein M represents an alkali metal, m represents 0 or an integer of from 1 to 2, and n represents 0 or an integer of from 1 to 3 will be described in detail. The present process is featured in that AADA is reacted with any of metal oxides, metal hydroxides, metal carbonates, metal hydrogencarbonates, ammonium hydroxide, ammonium carbonate, ammonium hydrogencarbonate or organic amine compounds. According to the present process, an AADA containing no alkali metal ions such as sodium ions is used as a material, and by-products such as alkali metal salts are not formed.

The AADA to be used in the present process is preferably one obtained by removing alkali metal ions from an aqueous solution of AADA alkali metal salt by electrodialysis. The electrodialysis requires neither a regeneration procedure of a resin as in the use of an ion exchange resin nor crystallization and isolation of crystals of an AADA salt as in the addition of an organic solvent, and can reduce alkali metal ions from the aqueous solution of an AADA alkali metal salt with efficiency. Of the electrodialysis techniques, the process in which a hydrogen ion permselective membrane and a cation permeable membrane are arranged respectively on the anode and cathode sides is more preferred.

In the process for the production of a salt of an amino acid-N,N-diacetic acid represented by the formula (1) wherein M represents an alkali metal, m represents 0 or an integer of from 1 to 2, and n represents 0 or an integer of from 1 to 3, the reaction of an AADA with any of metal oxides, metal hydroxides, metal carbonates, metal hydrogencarbonates, ammonium hydroxide, ammonium carbonate, ammonium hydrogencarbonate or organic amine compounds should preferably be conducted at temperatures ranging from 40° C. to 100° C. If the reaction temperature is higher than 100° C., the AADA may be decomposed, or the solution become highly colored in the production of organic amine salts. As the AADA has a chelating activity, a metal compound is rapidly dissolved by adding a powdery metal compound while stirring at a normal stirring intensity.

The AADA to be used as a material for the process of producing a salt of an amino acid-N,N-diacetic acid represented by the formula (1) wherein M represents an alkali metal, m represents 0 or an integer of from 1 to 2, and n represents 0 or an integer of from 1 to 3 includes, but is not limited to, glutamic acid-N,N-diacetic acid, aspartic acid-N,N-diacetic acid, glycine-N,N-diacetic acid, α-alanine-N,N-diacetic acid, β-alanine-N,N-diacetic acid, serine-N,N-diacetic acid, and other AADAs; iminodisuccinic acid, ethylenediaminedisuccinic acid and other disuccinic acids. Of these compounds, an AADA, in particular glutamic acid-N,N-diacetic acid, is typically preferred.

As metal oxides to be used in the process of producing a salt of an amino acid-N,N-diacetic acid represented by the formula (1) wherein M represents an alkali metal, m represents 0 or an integer of from 1 to 2, and n represents 0 or an integer of from 1 to 3, any of metal oxide generally used can be employed, such as potassium oxide, magnesium oxide, calcium oxide, zinc oxide, copper oxide, manganese oxide and other metal oxides.

The metal hydroxides include, but are not limited to, potassium hydroxide, iron hydroxide, iron oxide hydrate, magnesium hydroxide, calcium hydroxide, zinc hydroxide, copper hydroxide, and manganese hydroxide.

Any of generally employed metal carbonates can be used as the metal carbonates, including potassium carbonate, calcium carbonate, cobalt carbonate, and other metal carbonates.

As the metal hydrogencarbonates, use can be made of, for example, potassium hydrogencarbonate, calcium hydrogencarbonate, and cobalt hydrogencarbonate.

Organic amine compounds to be used in the present invention include, but are not limited to, monomethylamine, dimethylamine, trimethylamine, monoethylamine, diethylamine, triethylamine, and other alkylamines; monoethanolamine, diethanolamine, triethanolamine, monoisopropanolamine, dimethylethanolamine, and other alkanolamines; and pyridine.

The AADA salts obtainable by the process of the present invention include, for instance, calcium disodium glutamic acid-N,N-diacetate, an ammonium ferric salt of glutamic acid-N,N-diacetic acid, magnesium disodium glutamic acid-N,N-diacetate, and dimagnesium glutamic acid-N,N-diacetate.

Of the AADA salts, magnesium salts can be used as bleaching stabilizers. Such AADA magnesium salts are used as powders obtained by cooling, concentration, crystallization by the addition of a bad solvent, spray drying, freeze drying or another means. The magnesium salt of the amino acid-N,N-diacetic acid is low in hygroscopicity and is highly stable when stored. If the proportion of the magnesium compound to be reacted is less than 0.5 equivalent relative to 1 equivalent of the carboxyl group, the hygroscopicity increases and the resultant salt deliquesces and is liquefied. On the contrary, if 0.5 equivalent or more of the magnesium compound is reacted, the hygroscopicity is improved but excess magnesium compound does not react with the amino acid and should be removed by filtration, which deteriorates economical efficiency.

The bleaching agent composition comprises the AADA magnesium salt and an oxygen bleaching base. The oxygen bleaching base is one or more compounds selected from peroxides. Such peroxides include, but are not limited to, sodium peroxocarbonate, sodium peroxoborate, sodium peroxopolyphosphate, sodium peroxopyrophosphate, and sodium sulfate/sodium chloride/hydrogen peroxide adduct. The AADA magnesium salt is preferably a magnesium salt of an AADA, more preferably a magnesium salt represented by the formula (1), and particularly preferably a magnesium salt of glutamic acid-N,N-diacetic acid. The proportion of the AADA magnesium salt relative to sodium peroxocarbonate or another peroxide should preferably fall in the range from 0.1% to 20% by weight, and more preferably from 1% to 10% by weight. The bleaching agent composition according to the present invention is preferably used by blending a powdery AADA magnesium salt and an oxygen bleaching base, and dissolving the mixture in water before use. According to the present invention, where the proportion of magnesium salt in AADA is adjusted to 0.5 to 1 equivalent relative to the carboxyl group, a bleaching agent composition having a satisfactory storage stability can be obtained. In particular, dimagnesium glutamic acid-N,N-diacetate is desirable.

A solution of a ferric salt of an AADA is preferably produced, by electrodialyzing an aqueous solution of an alkali metal salt of an AADA with the use of a hydrogen ion permselective membrane on the anode side and a cation permeable membrane on the cathode side to give an AADA, and reacting the AADA with an iron oxide or metallic iron. According to the present process, the AADA obtained through electrodialysis, in which specific permeable membranes are placed respectively in specific locations, is used as a material, and therefore a ferric salt solution of AADA can be produced with efficiency without the formation of by-products.

Depending on the species of the material, a solution mixture of a ferrous salt and a ferric salt may be formed. In this case, such a ferrous salt AADA is subject to oxidation treatment according to necessity to give a ferric salt.

The conditions of the electrodialysis are identical to those wherein electrodialysis is performed by using a hydrogen ion permselective membrane on the anode side and a cation permeable membrane on the cathode side.

The reaction temperature for converting the AADA to an iron salt should preferably range from 50° C. to 80° C. Regarding the lower limit of the temperature, it is more preferably 60° C. or higher. Regrading the upper limit, it is more preferably 70° C. or lower. If the reaction temperature is higher than 80° C., the AADA may be pyrolyzed, or may be oxidized and decomposed by oxidation of iron (III). On the contrary, if it is lower than 50° C., the reaction rate with an iron oxide or metal oxide may be decreased.

AADAs to be used in the present invention include, but are not limited to, glutamic acid-N,N-diacetic acid, aspartic acid-N,N-diacetic acid, glycine-N,N-diacetic acid, α-alanine-N,N-diacetic acid, β-alanine-N,N-diacetic acid, and serine-N,N-diacetic acid, of which glutamic acid-N,N-diacetic acid can advantageously be used.

Iron oxides to be used in the present invention include, but are not limited to, ferrous oxide, ferric oxide, iron oxide hydrate, tri-iron tetraoxide. Each of these compounds can be used independently or in combination. Among them, tri-iron tetraoxide is advantageously employed from the viewpoint of reaction rate. Iron oxides and iron oxide hydrate can advantageously be used as well. This is because they may require no oxidation treatment in a later process and thus does not invite decomposition of the ferric salt of AADA in such an oxidation treatment, although they are somewhat lower in reaction rate than tri-iron tetraoxide. The reaction rate can be increased by the combination use with a powdery metallic iron or a reducing agent, or by the decreasing of the particle diameter of the iron oxide.

When tri-iron tetraoxide is used, the obtained reaction mixture contains both a ferrous salt and a ferric salt. Even if iron(III) is used as a material, the reaction mixture will contain a ferrous salt coresident with a ferric salt in case that a reducing agent is employed concurrently. Such a product reaction mixture can be used as intact as an iron fertilizer for agricultural use, but it requires an oxidation treatment to be used as a photographic bleaching agent, because such a mixture must completely be converted into a ferric salt. The oxidation treatment can be performed according to any of conventional known processes, of which a process of oxidizing the salt by blowing air is most economical and preferred.

The solution of a ferric salt of an AADA should preferably be adjusted, prior to the oxidation treatment, to pH 2.0 to 5.0, and more preferably pH 3.0 to 4.0 by adding ammonia or an alkali metal hydroxide to the solution. This is because if the pH is lower than 2.0, the rate of the oxidation reaction may be decreased, on the contrary, if it is higher than 5.0, oxidative decomposition of the ferric salt of AADA during oxidation treatment may be increased. Naturally, addition of ammonia or the like is not required when the pH of the ferric solution of AADA is, as intact, within the above preferred range. The addition of these compounds is not required as well as in the case where a ferric salt solution of AADA being low in pH is required according to its application. Ammonia or an alkali metal hydroxide may be added after the oxidation treatment, when the solution should be adjusted to desired pH according to the application of the ferric salt of AADA.

Alkali metal hydroxides to be used include hydroxides of sodium, potassium and the like. Each of these hydroxides can be used singly or in combination. The molar equivalent (relative to the AADA) of the material iron to be used in the reaction should preferably fall in the range from 0.9 to 1.1, and more preferably from 0.95 to 1.05 equivalent. If the molar equivalent exceeds 1.1, the undissolved iron material must be removed by filtration, resulting in an increased work load and loss of the iron material. On the contrary, if the molar equivalent is less than 0.9, a large quantity of the AADA remains unreacted due to an insufficient supply of the iron material, resulting in a loss of materials.

When ammonia or an alkali metal hydroxide is added prior to the reaction, its amount is preferably equimolar amount to or less than that of the AADA. This is because the addition in an amount exceeding the equimolar amount may decrease the reaction rate between the AADA and the iron oxide.

The reaction mixture should be maintained at a temperature of equal to or lower than 70 degrees, and preferably equal to or lower than 60 degrees. When the temperature of the reaction mixture is higher than 70° C. and air is blown, the decomposition of the AADA may be increased.

As an oxidizing agent, use can be made of, for example, oxygen, ozone, hydrogen peroxide, persulfates, and organic peroxides, but the use of persulfates, organic peroxides and the like should be avoided when the product is used for applications where contamination of by-produced ions is disadvantageous.

Upon the completion of the oxidation treatment, a ratio of (AADA molarity/iron molarity) in the reaction mixture should be adjusted to 1.0–1.1. If the iron is in existence in an excess amount, iron hydroxide is precipitated during the storage of the ferric salt solution of AADA, or iron oxide is compounded in the crystals of the ferric salt of AADA, which causes cloudiness when the crystals are dissolved into a solution. On the contrary, if the AADA is in existence in an excess amount, the AADA is wasted. Therefore, it is preferable to adjust the molar ratio by incorporating an excess amount of the iron in the reaction mixture beforehand, and adding another portion of the solution of AADA, which has been electrodialyzed, to the reaction mixture.

In another preferred embodiment, crystals of an ammonium ferric salt of glutamic acid-N,N-diacetic acid are formed from a solution of an ammonium ferric salt of glutamic acid-N,N-diacetic acid by adjusting the solution to pH range 2.5–5.0, and more preferably to pH range 3.5–4.2 to crystallize the ammonium ferric salt of glutamic acid-N,N-diacetic acid, and separating the crystals.

Figure 6:
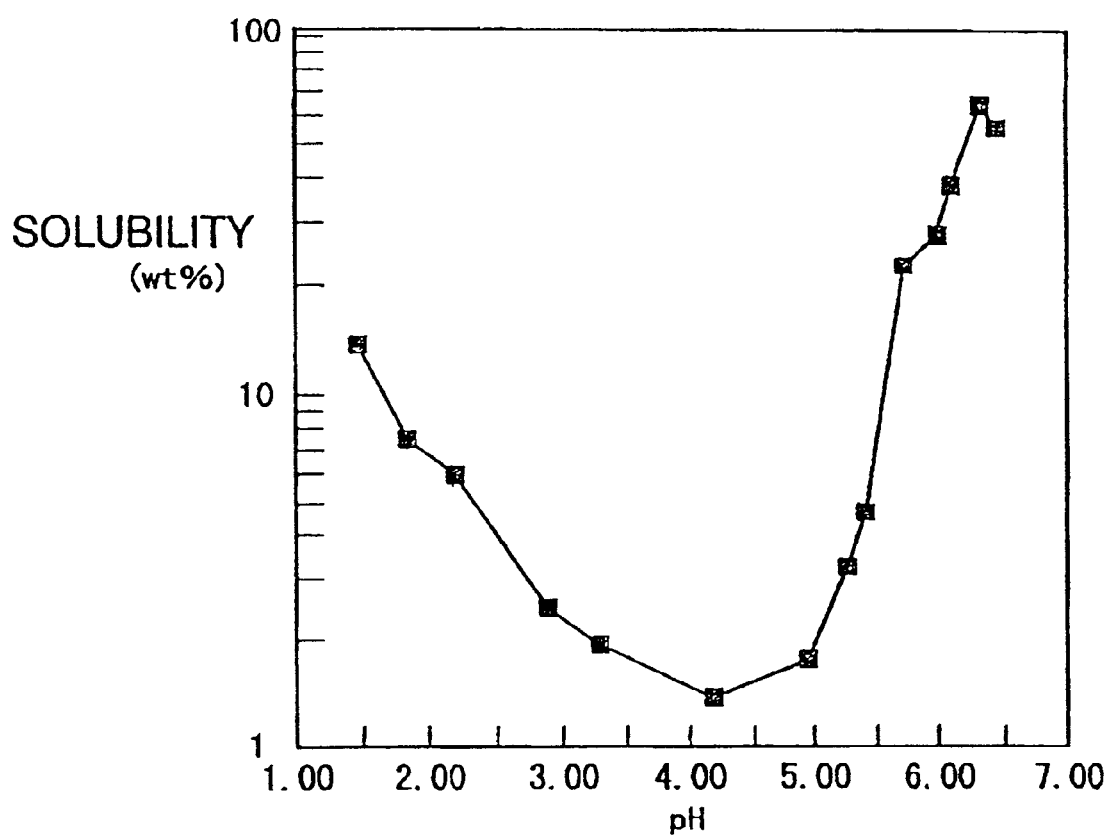
FIG. 6 is a graph showing the relationship between the solubility and the pH of a solution of an ammonium ferric salt of glutamic acid-N,N-diacetic acid.

FIG. 6 is a diagram showing the relationship between the pH and solubility of the solution of an ammonium ferric salt of glutamic acid-N,N-diacetic acid. This figure demonstrates that a plot of the solubility versus pH of an ammonium ferric salt of glutamic acid-N,N-diacetic acid describes an inverse parabola and attains the minimum at about pH 4.2. As the crystal of an ammonium ferric salt of glutamic acid.-N,N-diacetic acid comprises glutamic acid-N,N-diacetic acid, ferric oxide, and ammonium ion in a compositional ratio of 1:1:1, on the border of pH 4.2 (the pH where glutamic acid-N,N-diacetic acid, iron(III) and ammonium ion are in existence in a ratio of 1:1:1), the concentration of ammonium ion in a mother liquor increases and the pH of the solution increases with precipitation of crystals in a region where pH is higher than 4.2, i.e., the region where the ammonium ion is in exist in a large proportion. On the contrary, in a region where the pH is lower than 4.2, i.e., the region where the ammonium ion is in existence in a small proportion, I the concentration of the ammonium ion in the mother liquor decreases, and the pH of the solution decreases along with the precipitation of crystals. As the plot of the relationship between pH and solubility of the solution of an ammonium ferric salt of glutamic acid-N,N-diacetic acid describes an inverse parabola as described above, the solubility increases with an increasing pH in a region where the pH is high, and, it increases with a decreasing pH in a region where pH is low, and the precipitation of crystals ceases in both cases. Accordingly, even within the pH range where crystals should precipitate, a desired yield of crystal cannot be obtained in the vicinity of the upper and lower limits of the range. According to the production process for a crystal of an ammonium ferric salt of glutamic acid-N,N-diacetic acid, where the pH is adjusted to the range from 2.5 to 5.0, the yield of crystal can dramatically be improved than ever before.

To adjust the pH of the solution of an ammonium ferric salt of glutamic acid-N,N-diacetic acid, aqueous ammonia or an aqueous solution of glutamic acid-N,N-diacetic acid may be added.

The solution of an ammonium ferric salt of glutamic acid-N,N-diacetic acid can be prepared according to any process, but the solution of an ammonium ferric salt of glutamic acid-N,N-diacetic acid obtained by the process of electrodialyzing an aqueous solution of an alkali metal salt of glutamic acid-N,N-diacetic acid can advantageously be employed.

To increase the yield of crystal, additional conventional operations such as recycling of the filtrate, concentration, cooling, addition of an organic solvent can be performed. Furthermore, the addition of crystals of identical species to that of crystal of the ammonium ferric salt of glutamic acid-N,N-diacetic acid as seed crystals can enhance the precipitation of crystal of the ammonium ferric salt of glutamic.acid-N,N-diacetic acid and can facilitate the separation operation.

The precipitated crystals are separated by a conventional separation process such as centrifugal separation, is washed with water and dried to give crystals of an ammonium ferric salt of glutamic acid-N,N-diacetic acid. The crystals were high in purity free of hygroscopicity and were satisfactory in biodegradability.

EXAMPLES

The present invention will be further illustrated in detail with reference to several inventive examples and comparative examples below, which are not directed to limiting the scope of the invention.

Example 1

FIG. 1 is a schematic diagram illustrating an electrodialyzer (Asahi Glass Co., Ltd.: DU-Ob type electrolytic bath) used in the present example. An aqueous acid solution (sulfuric acid solution) is circulated with a circulation pump (not shown) from a reservoir (not shown) through an intermembranous space indicated as "aqueous acid solution" in the figure and is returned to the reservoir. The concentration of sulfuric acid is 10 wt %. An electrode solution is fed with a circulation pump (not shown) from a reservoir (not shown) to both electrode cells and circulated to the reservoir. A cell indicated as "sample" in the figure is a cell into which a sodium AADA solution flows, and the sodium AADA solution is circulated with a circulation pump (not shown) from a reservoir (not shown) through an intermembranous space of the electrodialyzer to the reservoir.

Hydrogen ion permselective membranes (Asahi Glass Co., Ltd.: Selemion HSV, indicated as "H" in the figure), cation permeable membranes (Asahi Glass Co., Ltd.: Selemion CMV, indicated as "C" in the figure) and a thick-film cation permeable membrane (Asahi Glass Co., Ltd.: Selemion CMT, indicated as "T" in the figure) were placed in the arrangement shown in FIG. 1. The number of effective sets for dialysis was eight sets and the effective area of each membrane was 209 $cm^2$. The electrodialysis was performed in the following manner: A total of 18.0 kg of a solution of tetrasodium glutamic acid-N,N-diacetate (tetrasodium glutamic acid-N,N-diacetate: 35.2%, Na concentration: 10.2%, pH 12.0), initially 40 kg (10%) of a sulfuric acid solution (it was replaced with two portions of an equivalent amount of the sulfuric acid solution) and 10 kg of an electrode solution (2% sulfuric acid) were placed into individual reservoirs, and electrodialysis was performed while circulating each solution with a pump. A current of 684 AHr was fed for 52 hours with a constant voltage of 15 V. The maximum current was 15 A at an early stage but it decreased to 9 A at a latter stage. The obtained solution of glutamic acid-N,N-diacetic acid was 13.2 kg (glutamic acid-N,N-diacetic acid: 34.2%, Na concentration: 0.007%, pH 1.1) and sulfuric ions were contaminated in a proportion of 0.2% in terms of $Na_2SO_4$. The yield of GLDA was 95.4%.

Example 2

FIG. 2 is a schematic diagram illustrating an electrodialyzer (Asahi Glass Co., Ltd.: MicroacilyzerEx3) used in the present example. An aqueous solution of tetrasodium salt GLDA (indicated as "sample" in the "figure") is circulated with a circulation pump (not shown) from a reservoir (not shown) through an intermembranous space between cation permeable membranes ("K5O1SB" manufactured by Asahi Chemical Industry Co., Ltd., indicated as "C" in the figure) to the reservoir. A 2N sulfuric acid (indicated as "aqueous acid solution" in the figure) is circulated in a next cell separated by a cation permeable membrane on the anode side, and water is circulated in another next cell separated by another cation permeable membrane on the cathode side. As an electrode solution, a 1N sodium sulfate is used.

Electrodialysis was carried out while circulating 1 kg of a solution of tetrasodium glutamic acid-N,N-diacetate (tetrasodium glutamic acid-N,N-diacetate: 40.1%, Na concentration: 11.6%, pH 13.0) through this device by a pump to make the pH of the solution to 7 over 6 hours. The sodium concentration of the solution was decreased to 8.8 wt %.

As a result, a 40.3 wt % solution of a trisodium monohydroqen salt of glutamic acid-N,N-diacetic acid was obtained. The yield of the salt was 99%. The overall results are shown in Table 2.

Example 3 to 8

Electrodialysis was performed in the same manner as in Example 1, according to conditions of the target to be electrodialyzed and electrodialysis time period as indicated in Table 1. results are set forth in Table 2.

TABLE 1

| Example | Target Compound | Concentration wt % | Weight kg | Na Ion Concentration | Treating Time |
|---|---|---|---|---|---|
| 1 | GLDA-4Na | 40.1 | 1 | 11.6 | 6 |
| 2 | GLDA-4Na | 40.1 | 1 | 11.6 | 3 |
| 3 | GLDA-4Na | 40.1 | 1 | 11.6 | 15 |
| 4 | ASDA-4Na | 35.5 | 1 | 10.5 | 7 |
| 5 | SDA-3Na | 42.7 | 1 | 11.0 | 15 |
| 6 | αADA-3Na | 25.9 | 1 | 6.9 | 3 |
| 7 | βADA-3Na | 24.9 | 1 | 6.8 | 3 |
| 8 | IDS-4Na | 36.1 | 1 | 10.3 | 6 |

TABLE 2

| Example | Produced Compound | Concentration wt % | Yield % | Na Ion Concentration | pH |
|---|---|---|---|---|---|
| 1 | GLDA-3Na1H | 40.3 | 99 | 8.8 | 7 |
| 2 | GLDA-2Na2H | 39.8 | 99 | 5.9 | 4 |
| 3 | GLDA-4H | 39.5 | 97 | 0.1 | <1 |
| 4 | ASDA-2Na2H | 35.0 | 98 | 5.5 | 4 |
| 5 | SDA-3H | 41.9 | 96 | 0.2 | <1 |
| 6 | αADA-2Na1H | 25.0 | 98 | 4.4 | 6 |
| 7 | βADA-2Na1H | 24.3 | 99 | 4.5 | 6 |
| 8 | IDS-2Na2H | 35.9 | 98 | 5.1 | 4 |

GLDA-3Na1H: solution of trisodium salt of glutamic acid-N,N-diacetic acid
GLDA-2Na2H: solution of disodium salt of glutamic acid-N,N-diacetic acid
GLDA-4H: solution of glutamic acid-N,N-diacetic acid
ASDA-2Na2H: solution of sodium salt of aspartic acid-N,N-diacetic acid
SDA-3H: solution of serine-N,N-diacetic acid
αADA-2Na1H: solution of disodium salt of α-alanine-N,N-diacetic acid
βADA-2Na1H: solution of disodium salt of β-alanine-N,N-diacetic acid
IDS-2Na2H: solution of disodium salt of iminodisuccinic acid diacetic acid Example 9

FIG. 3 is a schematic diagram illustrating an electrodialyzer (Asahi Glass Co.g Ltd.: Microacilyzer S3) to be used in the present example. An aqueous solution of tetrasodium GLDA (indicated as "sample" in the figure) is fed with a circulation pump (not shown) from a reservoir (not shown) through a space between a cation permeable membrane and an anion permeable membrane ("AC-110-800" cartridge type, manufactured by Asahi Chemical Industry Co., Ltd., indicated respectively as "C" and "A" in the figure), and is circulated to the reservoir. An anion permeable membrane is used as a permeable membrane on the anode side, and a cation permeable membrane is used as a permeable membrane on the cathode side. A 2 N sulfuric acid (indicated as "aqueous acid solution" in the figure) is respectively circulated in next chambers each separated by the anion permeable membrane or cation permeable membrane. As an electrode solution, a 1 N sodium sulfate is used.

Initially, 100 g of concentrated hydrochloric acid was added to 1 kg of a sample solution of tetrasodium salt of glutamic acid-N,N-diacetic acid (tetrasodium salt of glutamic acid-N,N-diacetic acid: 35.2%, Na concentration: 10.2%, pH 12.0) to adjust the resultant solution to pH 7.

Next, electrodialysis was conducted while circulating the neutralized sample with a pump. After 3-hour dialysis, the Cl ion concentration in the solution was reduced to 5 ppm (by silver nitrate titration).

As a result, a 36.1 wt % solution of trisodium monohydrogen, salt of glutamic acid-N,N-diacetic acid was obtained in a yield of the salt of 99%. The final sodium concentration was 7.5 wt %, and the pH of the solution was 7. The proportion of sodium glycolate was reduced from 6.5 wt % to 1.1 wt %. The overall results are shown in Table 4.

Examples 10 to 12

Electrodialysis was performed in the same manner as in Example 9, according to conditions for the target to be electrodialyzed and electrodialysis time period as indicated in Table 3. The results are set forth in Table 4.

Comparative Example 1

To the solution of tetrasodium glutamic acid-N,N-diacetate used in Example 2 was added hydrochloric acid and the solution was adjusted to pH 1 to precipitate sodium chloride. The precipitated sodium chloride was removed by filtration and a remained filtrate was added to threefold volume of methanol to precipitate glutamic acid-N,N-diacetic acid. The obtained solid glutamic acid-N,N-diacetic acid had a purity of 30% with the balance of sodium chloride. As a result, the yield of glutamic acid-N,N-diacetic acid was 40%.

Comparative Example 2

To the solution of a tetrasodium salt of aspartic acid-N,N-diacetic acid used in Example 5 was added sulfuric acid to adjust the solution to pH 4, and the resultant solution was added to threefold volume of methanol. The precipitated solid disodium salt of aspartic acid-N,N-diacetic acid had a purity of 30% with the balance of sodium sulfate. The yield of the disodium salt of aspartic acid-N,N-diacetic acid was 45%.

Comparative Example 3

To 1 kg of the solution of tetrasodium glutamic acid-N,N-diacetate used in Example 2 was added an H type ion exchange resin IRA-120B (manufactured by Organo Co., Ltd.) in a batch system with stirring until the solution became pH 4. About 1 liter of the ion exchange resin was used. Subsequently, the resin was removed by filtration to give a solution of disodium glutamic acid-N,N-diacetate. The disodium salt of glutamic acid-N,N-diacetic acid was wasted due to attachment to the resin, and its yield was 80%.

TABLE 3

| Example | Target Compound | Concentration wt % | Weight kg | Na Ion Concentration | Treating Time |
|---|---|---|---|---|---|
| 9 | GLDA-4Na | 35.2 | 1 | 10.2 | 3 |
| 10 | GLDA-4Na | 30.5 | 1 | 8.8 | 6 |
| 11 | ASDA-4Na | 31 | 1 | 9.1 | 6 |
| 12 | EDDS-4Na | 20 | 1 | 9.1 | 10 |

EDDS-4Na: solution of tetrasodium ethylenediaminedisuccinate

TABLE 4

| Ex. | Produced Compound | Concentration wt % | Yield % | NA Ion Concentration | pH | Remarks |
|---|---|---|---|---|---|---|
| 9 | GLDA-3Na1H | 36.1 | 99 | 7.5 | 7 | sodium glycolate 6.5% → 1.1% |
| 10 | GLDA-2Na2H | 33.7 | 98 | 4.7 | 4 | sodium glycolate 5.5% → 4.5% |
| 11 | ASDA-2Na2H | 32.5 | 98 | 4.4 | 4 | sodium glycolate 2.1% → 1.0% |

TABLE 4-continued

| Ex. | Produced Compound | Concentration wt % | Yield % | NA Ion Concentration | pH | Remarks |
|---|---|---|---|---|---|---|
| 12 | EDDS-2Na2H | 20.2 | 98 | 4.2 | 4 | sodium bromide 11% → 0.2% |

EDDS-2Na2H: solution of disodium ethylenediaminedisuccinate

According to Example 1 corresponding to the process wherein electrodialysis is performed using a hydrogen ion permselective membrane on the anode side and a cation permeable membrane in the cathode side, glutamic acid-N,N-diacetic acid was obtained in a very high yield of 95.4%. Examples 2 to 8 provided target product compounds in remarkably higher yields than comparative examples. Examples 9 to 12 gave target product compounds in such high yield as in Examples 2 to 8. According to Examples 9 to 12, sodium glycolate, sodium bromide or another by-product formed by the neutralization reaction could be removed.

Example 13

To 1000 g (1.141 mol) of the solution of glutamic acid-N,N-diacetic acid obtained in Example 1 was added 118.2 g (1.141 mol) of calcium carbonate over 30 minutes. After the completion of addition, the mixture was aged at 80 degrees for 1 hour to remove dissolved carbon dioxide. A total of 93.1 g (2.282 mol) of sodium hydroxide was added to the mixture to adjust to pH 7.5, and a trace turbid in the mixture was removed by filtration to give 1150 g of a transparent solution of calcium disodium glutamic acid-N,N-diacetate. The solution contained 3.98% of calcium, which was of a quality that can directly be used as a calcium solution for agricultural application. In this connection, the proportion of calcium was analyzed by calcining the solution in an electric furnace, dissolving the burned product in hydrochloric acid, and analyzing the proportion through chelatometric titration.

The solution was dried with a spray drier to give 458 g of a fine powder free of hygroscopicity. The powder was readily dissolved in water to regenerate a transparent aqueous solution. The powder contained 9.98% of calcium.

To determine the biodegradability, a biodegradability test was conducted in the following manner: A sample was diluted with water to a chemical oxygen demand (COD) of 500 ppm, and the diluted sample was subjected to a biodegradability test in a compact aeration type activated sludger for 7 days using an activated sludge sampled from an activated-sludging facility of a chemical plant as a seed. The results are set forth in Table 7.

Example 14

To 1000 g (1.141 mol) of the solution of glutamic acid-N,N-diacetic acid obtained in Example 1 was added 138.6 g (2.282 mol) of 96% magnesium hydroxide over 5 minutes, and the resultant mixture was stirred at 80° C. for 30 minutes to give a transparent solution of pH 8.5. The equivalent of the magnesium compound relative to 1 equivalent of carboxyl group calculated from the charging proportion of the material was 0.5 equivalent. The solution was spray-dried with a desktop spray drier to give 468 g of a powder. The powder was placed in a desiccator (relative humidity: 80%), in which a saturated ammonium chloride solution at 40° C. was charged, and the time until the powder deliquesced was determined. The results are shown in Table 5.

Comparative Example 4

As a comparative example, 104.0 g (1.712 mol) of 96% magnesium hydroxide was added over 5 minutes to 1000 g (1.141 mol) of a solution of glutamic acid-N,N-diacetic acid, and the resultant mixture was stirred at 80° C. for 30 minutes to give a transparent solution. The solution was adjusted to pH 8.5 by adding 174 g of a 25% sodium hydroxide aqueous solution over 10 minutes. The equivalent of the magnesium compound relative to 1 equivalent of carboxyl group calculated from the charging proportion of the material was 0.375 equivalent. The solution was spray-dried with a desktop spray drier to give 477 g of a powder.

The above procedure was repeated, except that the charging proportion of magnesium hydroxide was reduced and the pH was adjusted to 8.5, to give powders each containing 0.250 equivalent and 0.125 equivalent of a magnesium compound relative to 1 equivalent of carboxyl group.

These powders were each placed in a desiccator (relative humidity: 80%), in which a saturated ammonium chloride solution at 40° C. was charged, and the time periods until the powders deliquesced were determined. The results are shown in Table 5.

TABLE 5

|  | Magnesium Equivalent | Time until Deliquesced (hr) |
|---|---|---|
| Example 14 | 0.500 | no deliquescence |
| Comp. Ex. 4 | 0.375 | 10 |
|  | 0.250 | 7 |
|  | 0.125 | 4 |

The magnesium salt of an amino acid according to Example 14 did not deliquesced. However, magnesium salts each containing not higher than 0.5 equivalent of a magnesium compound relative to 1 equivalent of carboxyl group deliquesced, and the time period for deliquescence decreased with a decreasing amount of a magnesium compound to be reacted.

Examples 15 to 20 and Comparative Examples 5 to 7

A bleaching agent composition containing 95% by weight of sodium peroxocarbonate and 5% by weight of a magnesium salt of an amino acid was dissolved in a proportion of 2% by weight in an aqueous solution containing 0.1 ppm of a metal ion (copper, manganese or iron) at 92° C., and the concentration of sodium peroxocarbonate after a lapse of a given period was determined, and a residual rate of sodium peroxocarbonate [(concentration after a lapse of a given period)/(initial concentration)×100] was calculated. The results are set forth in Table 6.

TABLE 6

| | | Species of Metal | Residual Rate of Sodium Peroxocarbonate (%) Elapsed Time (min) | | | | |
|---|---|---|---|---|---|---|---|
| Ex. | Amino Acid | Ion | 0 | 5 | 10 | 20 | 40 |
| Ex. 15 | Mg/GLDA mole ratio = 1.0 | Cu | 100.0 | 67.0 | 53.0 | 42.5 | 36.2 |
| Ex. 16 | Mg/GLDA mole ratio = 2.0 | Cu | 100.0 | 91.0 | 86.6 | 78.1 | 74.4 |
| Ex. 17 | Mg/GLDA mole ratio = 1.0 | Mn | 100.0 | 66.9 | 53.0 | 39.8 | 25.4 |

TABLE 6-continued

| | Amino Acid | Species of Metal Ion | Residual Rate of Sodium Peroxocarbonate (%) Elapsed Time (min) | | | | |
|---|---|---|---|---|---|---|---|
| Ex. | Magnesium Salt | | 0 | 5 | 10 | 20 | 40 |
| Ex. 16 | Mg/GLDA mole ratio = 2.0 | Mn | 100.0 | 90.4 | 82.9 | 75.3 | 61.8 |
| Ex. 19 | Mg/GLDA mole ratio = 1.0 | Fe | 100.0 | 28.5 | 20.3 | 17.9 | 17.0 |
| Ex. 20 | Mg/GLDA mole ratio = 2.0 | Fe | 100.0 | 92.2 | 84.9 | 82.5 | 79.5 |
| Comp. Ex. 5 | GLDA-Na | Cu | 100.0 | 53.5 | 35.2 | 16.7 | 6.4 |
| Comp. Ex. 6 | GLDA-Na | Mn | 100.0 | 57.3 | 33.5 | 12.9 | 3.6 |
| Comp. Ex. 7 | GLDA-Na | Fe | 100.0 | 9.0 | 2.8 | 1.1 | 0.3 |

Example 21

To 1000 g (1.141 mol) of the solution of glutamic acid-N,N-diacetic acid used in Example 14 were added 69.8 g (1.027 mol) of a 25% aqueous ammonium solution and 90.4 g (1.164 mol) of tri-iron tetraoxide, and were reacted at 60 degrees for 8 hours. Unreacted tri-iron tetraoxide was removed by filtration from the reaction mixture, and the resultant reaction mixture had pH of 3.4 and contained 1.9% of iron (II).

The reaction mixture was cooled to 25° C., and air was blown into the cooled reaction mixture with a diffuser to oxidize and lessen the content of iron(II) to 0.01%. The obtained solution of an ammonium ferric salt of glutamic acid-N,N-diacetic acid had a weight of 1130 g, an iron concentration (analyzed by potassium iodide-sodium thiosulfate titration) of 33.0% (1.119 mol), a GLDA concentration (analyzed by adding an alkali to remove iron and subjecting to chelatometric titration) of 31.6% (1.072 mol) and pH of 3.2. The yield of ammonium ferric salt of GLDA obtained by the neutralization reaction and oxidation treatment was 94.0%. Separately, a biodegradability test was performed in the same manner as in Example 14, and the results are shown in Table 7.

Example 22

A total of 51 g (0.058 mol) of a solution of glutamic acid-N,N-diacetic acid was added to 1130 g of the reaction mixture obtained in Example 21 to adjust the molar ratio of Fe/GLDA, and 15.6 g (0.230 mol) of a 25% aqueous ammonia was added to the mixture to adjust the pH. The solution of an ammonium ferric salt of glutamic acid-N,N-diacetic acid before crystallization had a weight of 1197 g, an iron concentration (analyzed by potassium iodide-sodium thiosulfate titration) of 31.1% (1.119 mol), a GLDA concentration (analyzed by adding an alkali to remove iron and subjecting to chelatometric titration) of 31.4% (1.130 mol), and pH of 4.0.

The reaction mixture was stirred at 25° C. for 18 hours to crystallize crystals, and the crystals were separated with a desktop centrifuge, washed with water and dried in air at 25° C. for 18 hours to give 294 g of a yellow-green crystal. The conversion rate of an ammonium ferric salt of glutamic acid-N,N-diacetic acid from the mother liquor to the crystal was 69.2%. Analyzed data for an ammonium ferric salt of glutamic acid-N,N-diacetic acid were as follows:

GLDA.Fe.NH$_4$.2H$_2$O content (potassium iodide-sodium thiosulfate titration): 97.2% (0.774 mol)

GLDA.Fe.NH$_4$.2H$_2$O content (chelatometric titration): 97.3% (0.775 mol)

NH$_4$ content (ion chromatography): 4.5% (0.735 mol)

SO$_4$ content (BaCl$_2$ addition): below the detection limit

Moisture (differential thermal analysis/referred to FIG. 4): 0.7 wt % (sample amount: 13.14 mg, moisture content: 0.10 mg)

Figure 4:
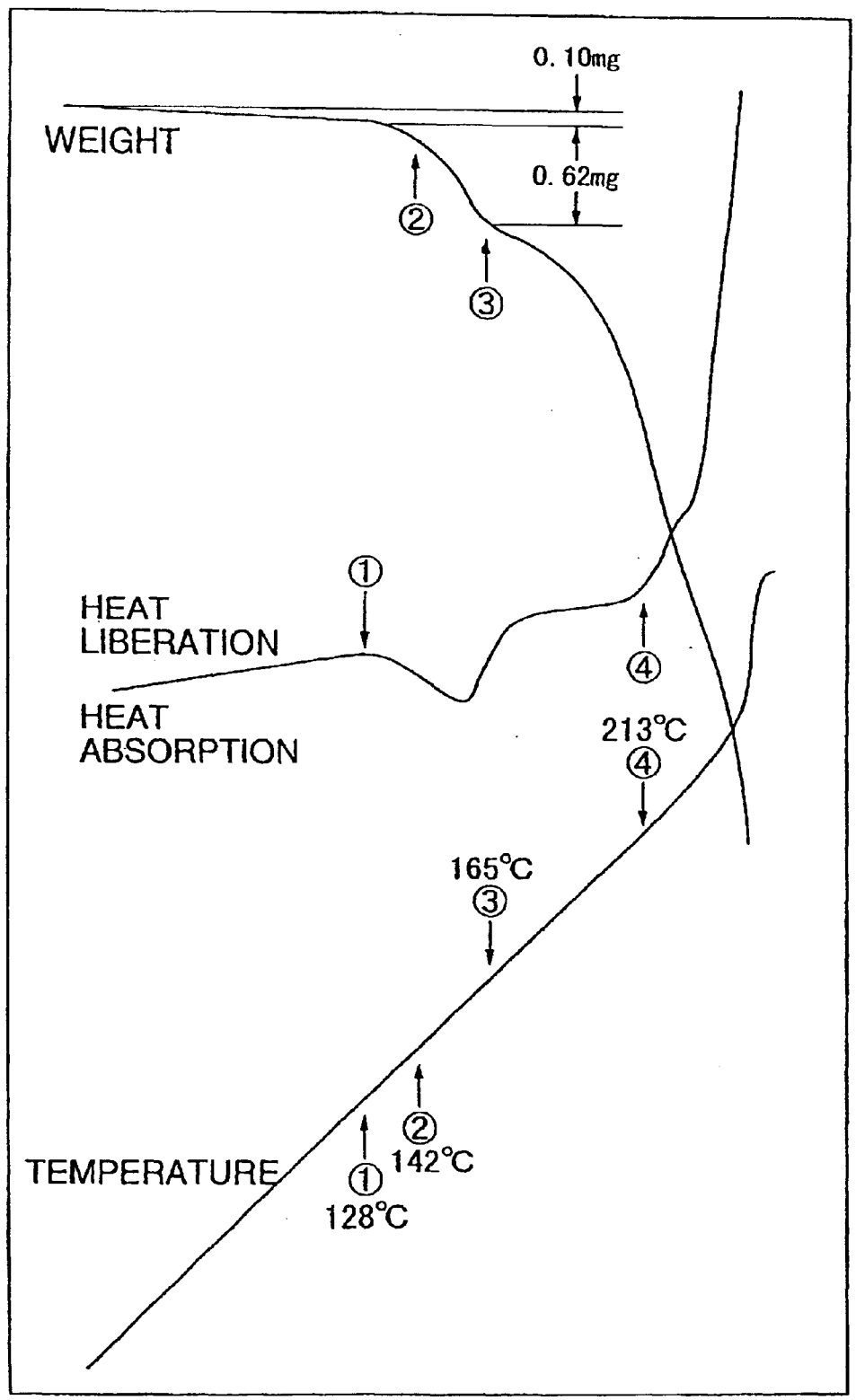
FIGS. 4 and 5 are respectively a differential thermal analysis chart and a Fourier transform infrared spectrophotometric (FT-IR) chart of an ammonium ferric salt of glutamic acid-N,N-diacetic acid obtained in Example 16.

Water of crystallization (differential thermal analysis): 0.97 H$_2$O was eliminated at 142 degrees or higher (indicated as ② in FIG. 4)

elimination of water of crystallization and decomposition occurred concurrently at 165 degrees or higher (indicated as ③ in FIG. 4)

Ignition temperature (differential thermal analysis): autogenous ignition at 213 degrees (indicated as ④ in FIG. 4)

pH (2.5%, 25 degrees): 4.1

Figure 5:
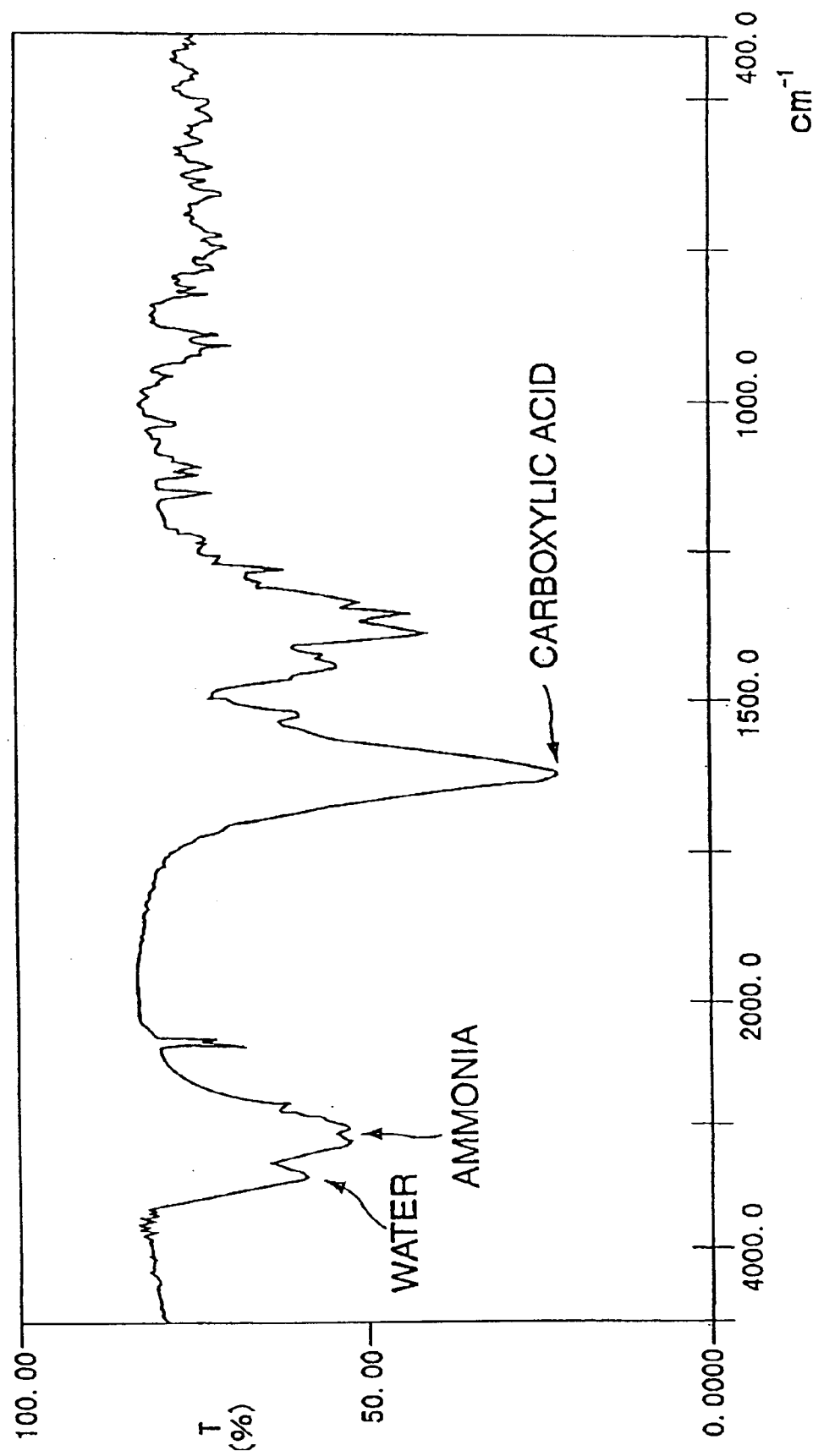

FT-IR analysis: shown in FIG. 5

An alkali component was added to a solution of the obtained crystal to remove the iron component, and the resultant solution was analyzed by high-performance liquid chromatography (HPLC) for organic acid analysis to verify that a chelator component corresponded to glutamic acid-N,N-diacetic acid. Separately, the content was determined by subjecting the solution to chelatometric titration thereby to verify that the chelator component and iron were chelate-reacted in a ratio of 1:1 within the range of analytical error. It was also verified that NH$_4$ ion was added in a ratio of 1:1 within the range of analytical error. In addition, an FT-IR chart (FIG. 5) of the crystal demonstrates that an absorption derived from a carboxylic acid group unique to a chelate iron salt and absorptions derived from ammonia and water.

The crystal was dried in air at 25° C. to reduce the moisture content to 0.7%. The obtained crystal was found to be a fluid crystal free of hygroscopicity.

Comparative Example 8

As a comparative example, ammonium ferric ethylenediaminetetraacetate was subjected to a biodegradability test. The results are shown in Table 7.

TABLE 7

| Sample | Decomposition Rate (%) |
|---|---|
| Calcium disodium glutamic acid-N,N-diacetic acid obtained in Ex. 13 | 100 |
| An ammonium ferric salt of glutamic acid-N,N-diacetic acid obtained in Ex. 21 | 79 |
| Ammonium ferric ethylenediaminetetraacetate | 0 |

Advantages

The process for the production of an AADA or a salt with equivalent or less of an alkali metal according to the present invention, where alkali metal ions are reduced from an aqueous solution of an AADA alkali metal salt by electrodialysis, requires no regeneration operation of a resin as in the case that an ion exchange resin is used and requires no crystallization-separation of crystals of an AADA salt as in the case that an organic solvent is added, and thus can provide an AADA salt in a much higher yield than ever before.

According to the process of the present invention, an amino acid salt having a secondary or tertiary amino group and three or more carboxyl groups, a high purity salt of an amino acid having a secondary or tertiary amino group and three or more carboxyl groups can be obtained with efficiency without by-production of unnecessary alkali metal salts.

The magnesium salt of an amino acid having a secondary or tertiary amino group and three or more carboxyl groups has an improved hygroscopicity and is hardly deliquesced.

The bleaching agent composition of the invention, where the magnesium salt of an amino acid is used, is excellent in storage stability.

According to the production process for a solution of a ferric salt of an AADA of the invention, a solution of a ferric salt of an AADA can be obtained with efficiency without the formation of unnecessary by-products.

In addition, according to the production process of a crystal of an ammonium ferric salt of glutamic acid-N,N-diacetic acid of the invention, the crystal can be obtained in a higher yield than conventional equivalents. The crystal obtained by the process has a higher purity than conventional equivalents and if free of hygroscopicity and is excellent in biodegradability.

What is claimed is:

1. A magnesium salt of an amino acid-N,N-diacetic acid, which is a salt of an amino acid-N,N-diacetic acid obtainable by a process comprising:

reducing alkali metal ions from an aqueous solution of an alkali metal salt of said amino acid-N,N-diacetic acid by electrodialysis to produce an amino acid-N,N-diacetic acid, wherein said alkali metal salt of an amino acid-N,N-diacetic acid is a salt represented by the following formula (1):

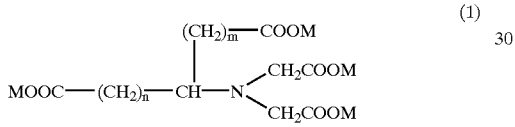

(1)

wherein M represents an alkali metal, m represents 0 or an integer of from 1 to 2, and n represents 0 or an integer of from 1 to 3; and reacting said amino acid-N,N-diacetic acid with a metal oxide, a metal hydroxide, a metal carbonate, a metal hydrogencarbonate, ammonium hydroxide, ammonium carbonate, ammonium hydrogencarbonate, or an organic amine compound.

wherein 0.5 to 1 equivalent of a magnesium compound is reacted with 1 equivalent of a carboxyl group.

2. A bleaching agent composition comprising the magnesium salt of amino acid-N,N-diacetic acid of claim 1 and an oxygen bleaching base.

3. A magnesium salt of an amino acid-N,N-diacetic acid, which is a salt of an amino acid-N,N-diacetic acid obtainable by a process comprising:

reducing alkali metal ions from an aqueous solution of an alkali metal salt of said amino acid-N,N-diacetic acid by electrodialysis to produce an amino acid-N,N-diacetic acid, wherein said alkali metal salt of an amino acid-N,N-diacetic acid is a salt represented by the following formula (1):

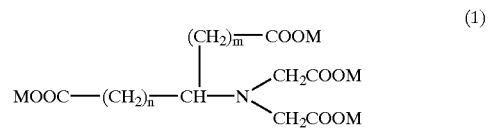

(1)

wherein M represents an alkali metal, m represents 0 or an integer of from 1 to 2, and n represents 0 or an integer of from 1 to 3; and reacting said amino acid-N,N-diacetic acid with a metal oxide, a metal hydroxide, a metal carbonate, a metal hydrogencarbonate, ammonium hydroxide, ammonium carbonate, ammonium hydrogencarbonate, or an organic amine compound wherein said amino acid-N,N-diacetic acid is glutamic acid-N,N-diacetic acid, and wherein 0.5 to 1 equivalent of a magnesium compound is reacted with 1 equivalent of a carboxyl group.

4. A bleaching agent composition comprising the magnesium salt of amino acid-N,N-diacetic acid of claim 3 and an oxygen bleaching base.

* * * * *